United States Patent
Parmigiani

[11] Patent Number: 6,113,555
[45] Date of Patent: Sep. 5, 2000

[54] DEVICE FOR WITHDRAWING BODY LIQUIDS AND FOR TRANSFERRING THEM INTO SAMPLE TUBES

[75] Inventor: Corrado Saverio Parmigiani, Correggio, Italy

[73] Assignee: C.G.M. S.p.A., Corregio, Italy

[21] Appl. No.: 09/188,362

[22] Filed: Nov. 10, 1998

[30] Foreign Application Priority Data

Nov. 13, 1997 [IT] Italy ................................ RE97A0088

[51] Int. Cl.[7] ..................................................... A61B 5/00
[52] U.S. Cl. .................. 600/579; 600/573; 600/581; 604/162; 604/246; 604/250
[58] Field of Search ................................. 600/573, 576, 600/577, 579, 581, 582; 604/93, 174, 175, 177, 178, 162, 264, 280, 192, 263, 246, 245, 250, 256

[56] References Cited

U.S. PATENT DOCUMENTS

| | | | |
|---|---|---|---|
| 2,876,768 | 3/1959 | Schultz | 600/577 |
| 2,998,956 | 9/1961 | Etten | 251/10 |
| 3,659,587 | 5/1972 | Baldwin | 128/2 F |
| 4,036,232 | 7/1977 | Genese | 600/576 |
| 4,280,509 | 7/1981 | Bethkenhagen et al. | 600/577 |
| 4,409,991 | 10/1983 | Eldridge | 604/246 |
| 5,147,329 | 9/1992 | Brannon | 600/577 |
| 5,242,417 | 9/1993 | Paudler | 604/192 |
| 5,309,924 | 5/1994 | Peabody | 600/573 |
| 5,342,753 | 8/1994 | Smith, Jr. | 435/2 |
| 5,533,984 | 7/1996 | Parmigiani | 604/162 |
| 5,552,118 | 9/1996 | Mayer | 600/573 |
| 5,556,599 | 9/1996 | Ahmed | 422/102 |
| 5,772,638 | 6/1998 | Utterberg et al. | 604/177 |

FOREIGN PATENT DOCUMENTS

| | | |
|---|---|---|
| 0692271 | 1/1996 | European Pat. Off. . |
| 296 20 187 U1 | 2/1997 | Germany ........................ 600/573 |
| 9116934 | 11/1991 | WIPO . |
| 9204867 | 4/1992 | WIPO . |

*Primary Examiner*—Cary O'Connor
*Assistant Examiner*—Charles Marmor, II

[57] ABSTRACT

A device having a protection cap defining a concavity, and a thin sharp-ended tubular stem joined to the cap and projecting into the concavity; the tubular stem being connected to elements for penetration into the human body or into body liquid containers; the device being also suitable for use in combination with sample tubes to be inserted into the concavity in the cap and having their interior chamber under vacuum and closed by a yieldable elastomeric plug able to seal an aperture produced by the tubular stem; the tubular stem being joined at one end to the interior concavity of the cap and constructed of a synthetic resinous material in one piece with the cap.

5 Claims, 4 Drawing Sheets

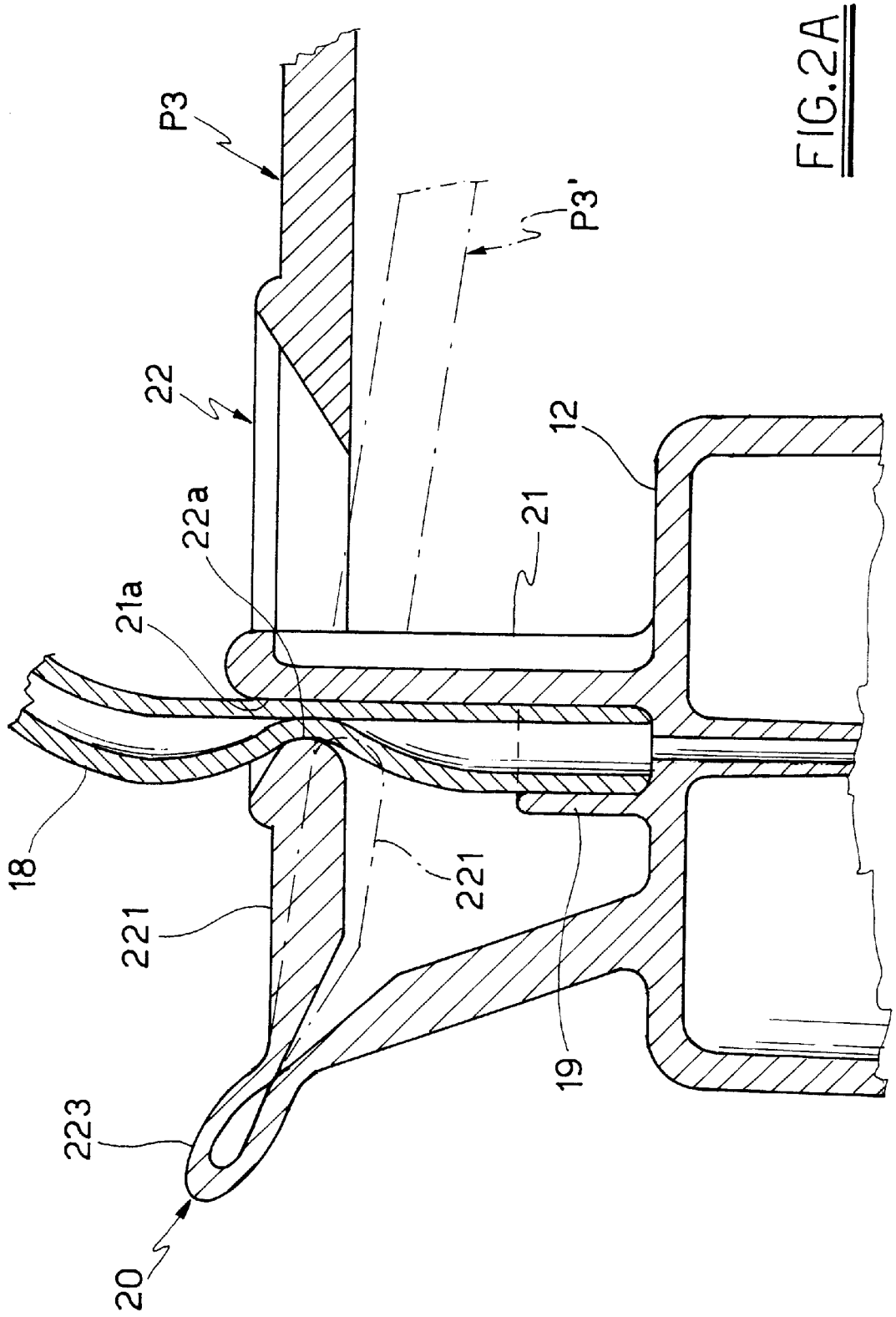

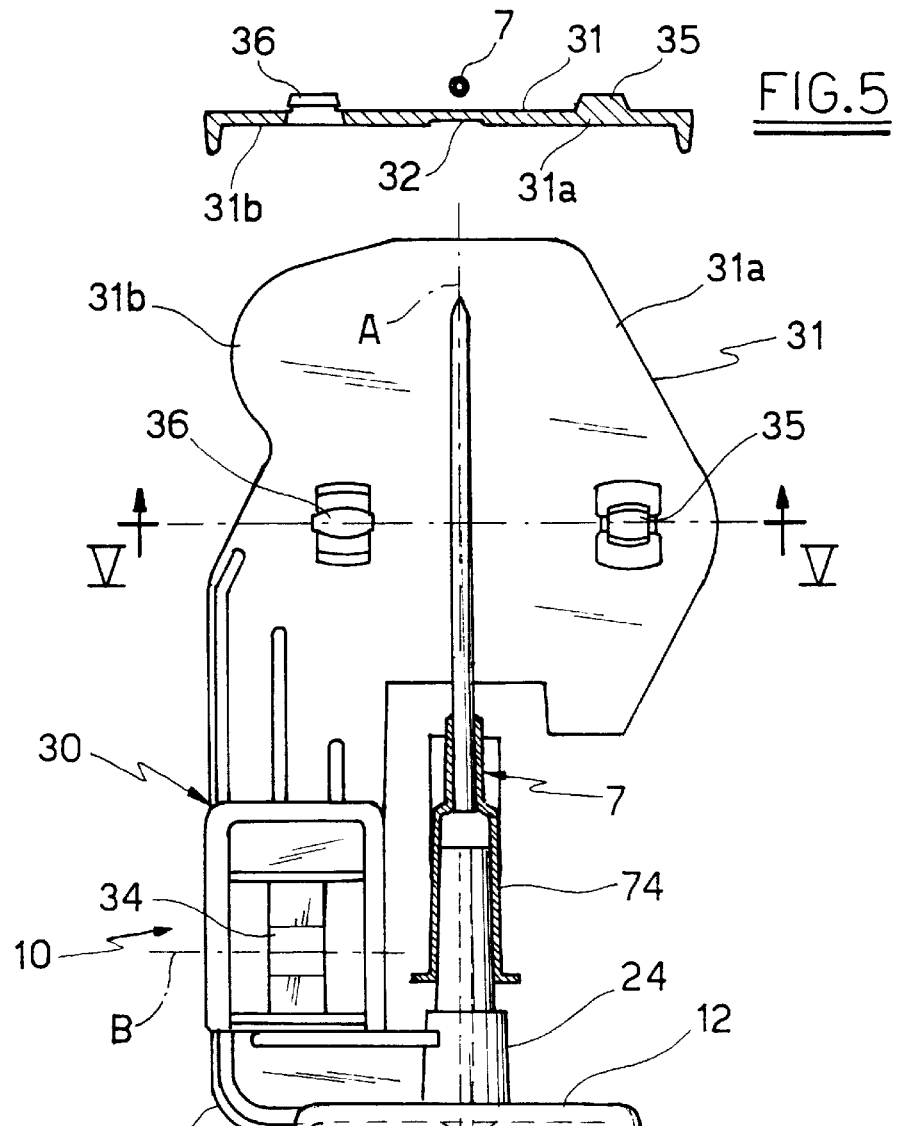
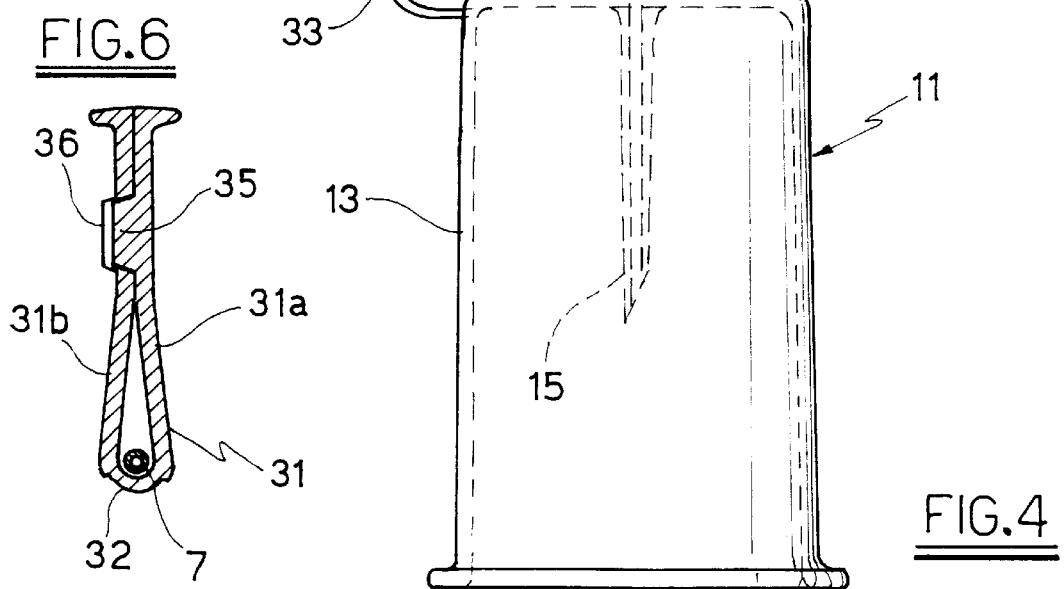

DEVICE FOR WITHDRAWING BODY LIQUIDS AND FOR TRANSFERRING THEM INTO SAMPLE TUBES

BACKGROUND OF THE INVENTION

The present invention relates to a device for withdrawing body liquids and transferring them into sample tubes.

Devices have been known for some time comprising a rigid protection cap defining a concavity, and a thin sharp-ended steel tubular stem screwed to the cap until it projects into its concavity.

The tubular stem is connected to means for penetrating the human body, in particular to an elastic flexible tube fixed to a foldable butterfly needle, or directly to an injection needle.

The device is suitable for use in withdrawing blood in combination with sample tubes to be inserted into the cap concavity and having their interior chamber under vacuum and closed by a yieldable elastomeric plug capable of sealing the aperture produced by the tubular needle stem (the plug being penetrated by the tubular needle stem and then sealing the channel produced by the tubular stem when the latter is extracted).

In use, the butterfly needle is inserted into a patient's vein, after which a sample tube is inserted into the cap such that the plug in the cap is traversed by the point of the tubular stem located within the cap. The vacuum present in the sample tube draws blood into the sample tube.

Hence the blood is drawn into the sample tube by an operation which is immediate and protected by virtue of the presence of the cap surrounding the point of the tubular stem.

After use the tubular stem is removed from the cap (which is reused) and disposed of in appropriate safety containers dedicated to needle collection.

Said operation carries however the risk that once separated from the cap, the tubular stem (which is soiled with the patient's blood) can prick the operator as its point is no longer enclosed by the cap.

A further drawback lies in the fact that in flowing into the sample tube, in particular in passing through the connection points between the tubular stem and its support member and between this latter and the external flexible conduit (or needle), the blood tends to "hemolyze", ie to break down its hemoglobins, so altering certain of its characteristics.

Moreover the tubular stem requires a valve which prevents the blood passing unless the the tubular stem is applied to a sample tube. The valve currently used consists substantially of a soft rubber cap enclosing the entire tubular stem.

Said valve has however various drawbacks.

A first drawback is that after the rubber cap has been penetrated a few times (to feed the blood into the sample tube) by the point of the tubular stem, it loses its sealing property and allows the blood to drip.

A further drawback is that the blood remaining in the cap inevitably soils the outer surface of the sample tube plug when the tubular stem is inserted through it.

SUMMARY OF THE INVENTION

An object of the present invention is to provide a device of the aforesaid type able to overcome said drawbacks.

BRIEF DESCRIPTION OF THE DRAWINGS

The present invention is described in detail hereinafter with the aid of the accompanying figures which illustrate a non-limiting embodiment thereof, wherein

FIG. 2A is an enlarged detail of FIG. 2;

FIG. 3 is a plan view of FIG. 2 from above;

FIG. 4 is an axial section taken through a second embodiment of the present invention;

FIG. 5 is a section taken along the plane V—V of FIG. 4 and

FIG. 6 shows a section of FIG. 5 in a folded configuration.

DETAILED DESCRIPTION OF THE INVENTION

The device of the invention (indicated overall by 10 in the figures) comprises a cylindrical protection cap 11 made of a rigid material defining a concavity defined by a cylindrical side wall 13 and a substantially flat upper end 12.

The device also comprises a thin sharp-ended tubular stem 15 in the shape of a usual syringe needle (thin tube with a lower point) joined to the cap end 12 at its upper end and projecting, with its point facing downwards, into the concavity of the cap 11. The tubular stem 15 is also connected to means for penetration into the human body (or into containers of body liquids).

According to the present invention, the tubular stem 15 is joined at one end to the surface of the internal concavity of the cap 11, and is constructed of a synthetic resin in one piece with the protection cap 11. In particular, the tubular stem 15 and the protection cap 11 are constructed of polyoxymethylene (acetal resin) by the high-pressure injection moulding of the fluid resin. Excellent results have been obtained with such a substance, known as "DELRIN[R]", manufactured by DUPONT DE NEMOURS.

Figure 1:
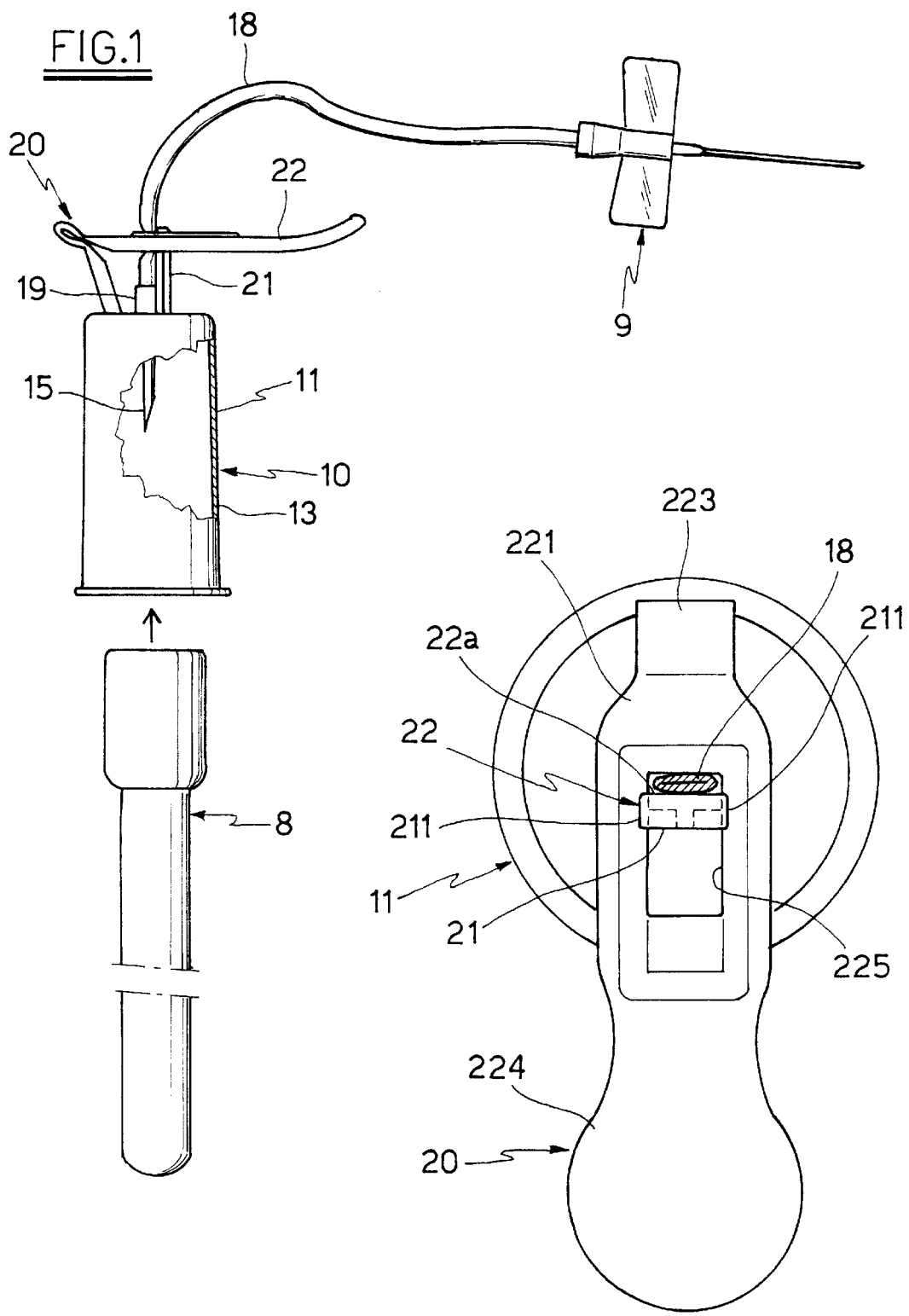
FIG. 1 is a general view of the device of the present invention and of other means with which the device is used.
Figure 2:
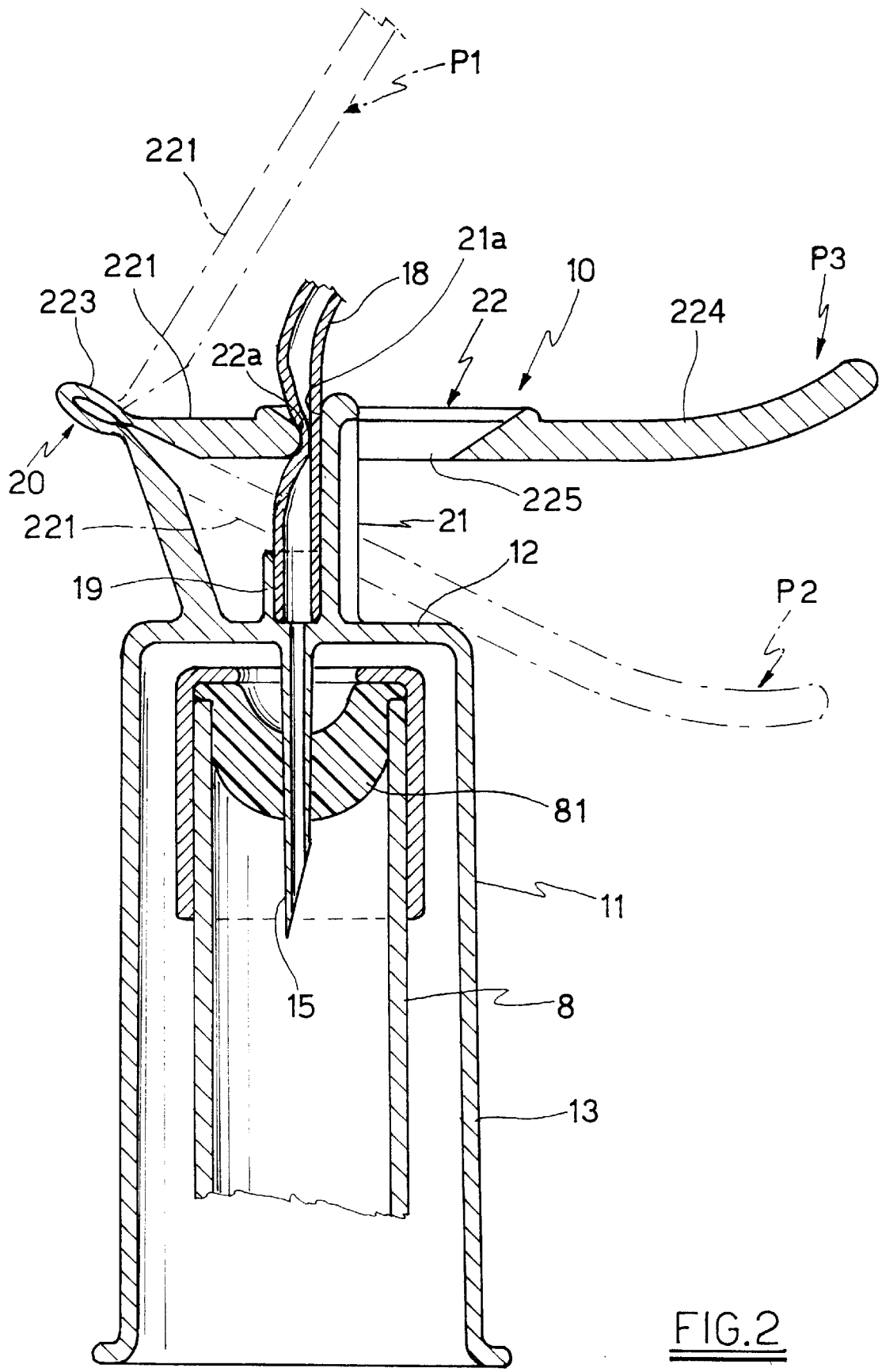
FIG. 2 is a sectional view taken, through the device of FIG. 1 along the axial plane and on an enlarged scale.

In the embodiment shown in FIGS. 1–3, the tubular stem 15 is connected, by an elastic flexible tube 18 external to the cap 11, to a needle 9 for penetration into a vein (or into other parts), in particular a needle of the "butterfly" type. On the end 12 of the cap 11 there is provided an upwardly projecting bushing 19 formed in one piece with the cap 11. The downstream end of the tube 18 is inserted into the cavity through the bushing 19 and is fixed into it, for example by adhesive.

In use, after inserting the needle 9, for example, into a patient's vein, the withdrawal can be carried out in combination with sample tubes 8 of a type (known per se) with their interior chamber under vacuum, and closed by a yieldable elastomeric plug which is penetrated by the tubular stem 15 and seals the penetration produced after the tubular stem has been extracted. The sample tubes 8 are of such a size as to be able to be inserted in the concavity in the cap 11.

For use, a sample tube 8 is inserted into the concavity in the cap 11 and pushed upwards to cause the tubular stem 15 to penetrate the plug 81 until the point of the tubular stem 15 enters the chamber in the sample tube 8 (as shown in FIG. 2). At this point, the vacuum in the chamber of the sample tube 8 draws blood through the conduit formed by the needle 9, the tube 18 and the tubular stem 15. On extracting the tubular stem from the sample tube 8, blood withdrawal is interrupted. Using this procedure, known per se, blood can be distributed to various sample tubes. According to the present invention, the device 10 contains a clamping means projecting upperly from the upper end 12 of the protection cap 11 and operable manually to close and open the passage through the elastically flexible tube 18. The clamping means is synthetic resin in one piece with the cap 11.

In the embodiment shown in the figures, the clamping means 20 comprises a rigid first projecting element 21, projecting vertically upwards from the upper surface of the cap and having a bearing region 21a for the tube 18.

The clamping means 20 also comprises a second element 22 bendable elastically on itself about a point 223 located substantially at the same level as said bearing region 21a.

The element 22 is formed in one piece with the rest of the device 10 and is shaped to define an elastically flexible thinner region defining a point of flexure 223 in an intermediate position. During its manufacture that element portion 221 beyond the point 223 is made to extend upwards from the point 223 (position P1 of FIG. 2).

Hence if bent downwards, the portion 221 normally tends to return upwards to its original position P1. The upper portion 221 has a pressing end 22a opposite the bearing region 21a for the first element 21. When the upper portion 221 is brought into a substantially horizontal position the end 22a presses and squeezes the tube 18 against the bearing region 21a of the first element 21 to close its passage (as shown in FIGS. 2 and 3). Downward rotation of the upper portion 221 of the second element 22 causes the pressing end 22a to withdraw from the bearing region 21a, and vice versa for upward rotation.

The element 22 is shaped to define, in one piece with the upper portion 221, a manually operated lever 224 extending beyond said pressing end 22a. In the portion 221 there is provided a slot 225 through which the tube 18 and the first element 21 pass. A transverse side of this slot defines said pressing end 22a, whereas the two longitudinal sides graze the tube 18 and the first element 21.

In use, the upper portion 221 is initially rotated downwards (in a clockwise direction in FIG. 2) to bend about the point 223 so that the pressing end 22a is lower than the point of flexure 223 (position P2 of FIG. 2).

At this stage, on releasing the lever 224 the portion 221 tends to move upwards (by rotating counter-clockwise) by virtue of the elastic characteristics of the material with which the point 223 is composed.

In moving upwards, the end 22a approaches the region 21a of the first element 21, to the extent of squeezing the tube 18 and completely closing its passage (position P3 of FIG. 2). When in said configuration, the upper portion 221 is virtually perpendicular to the axis of the tube 18.

Because of the special geometrical configuration of the means 20, the pressing end 22a presses against the tube 18 in a direction nearly tangential to the tube axis. When the pressure on the tube 18 is a maximum, the straight line joining the point of flexure 223 to the end 22a is virtually perpendicular to the axis of the tube 18. This means that a relatively small torque on the upper portion (produced by the elastic reaction of the second element 22 at the point of flexure 223) is sufficient to cause its end 22a to completely compress the cross-section of the tube 18. Consequently, if not operated, the means 20 automatically closes the passage through the tube 18.

On manually moving the lever 224 downwards (in a clockwise direction as far as the position P2), the end 22a withdraws from the bearing region 21a, so releasing the tube 18 which, being of elastic material, reopens its passage.

In detail (see FIG. 3), the upper end of the first element 21 comprises two lateral projections 211 which project outwards slightly beyond the profile of the slot 225 and hence hook the upper portion 221, to halt this in the position P3 before, by rotating upwards (counter-clockwise), it reaches the position P1. The means 20 is shaped such that the portion 221 is halted by the projection 211 slightly beyond that position (position P3' in FIG. 2) in which the end 22a commences effectively to close the passage through the tube 18. Consequently, when in use, on releasing the lever 224 the portion 221 rotates towards the position P3 as stated heretofore; slightly before reaching this position the end 22a completely compresses the tube 18 to close its passage (position P3'). However, because of the elasticity of the means 20 and tube 18, the portion 221 undergoes a further short upward travel until it halts in the position P3, abutting against the projections 221 (where it continues to maintain the passage through the tube 18 closed). During this short travel, although the passage through the tube 18 is maintained closed, the closure section shifts slightly upwards, consequently increasing the volume of the tube interior lying below this section. In other words a peristaltic pump effect is achieved, this effect producing a suction within the tubular stem 15 which is very useful for drawing any blood droplet present on the point of the tubular stem 15 upwards into the stem duct. To obtain this effect said short extent of travel from the position P3' to the position P3 need only be a few millimetres.

By virtue of its material of composition and of its manufacturing process, the entire device 10, including the clamping means 20, is of such relatively low cost that the entire device 10 can be disposed of after every use, while still remaining economically convenient. This avoids those dangers which the operator undergoes when disposing of a needle-type stem in the refuse when separated from its protection cap.

Moreover, as the tubular stem 15 is in one piece therewith, its passage channel is a single channel passing through both the tubular stem 15 and the end 12 of the cap without any discontinuity. This is very advantageous in avoiding any danger of damage to the structure of the hemoglobin present in the blood passing through this channel.

In addition, the clamping means 20 acts as an optimum valve for blocking the blood prior to the point of the tubular stem 15. Blood therefore cannot soil the outer surface of the plug 81 of sample tubes 8 when the tubular stem is inserted through them.

Furthermore the means 20 does not lose its facility for closing the passage through the tube 18 even after being operated a large number of times.

The blood passage can also be opened and closed when required, whether or not the tubular stem has been inserted through the plug of sample tubes 8.

Finally, the aforedescribed peristaltic pump effect draws in the blood located on the point of the tubular stem 15, to hence prevent blood soiling the plug of the sample tube 8 through which the tubular stem passes.

In the embodiment shown in FIGS. 4 and 5 the device 10 comprises insertion-connection means projecting from the upper surface of the protection cap to receive a syringe needle 7, and a means 30 in the form of a thin plate joined to the upper surface of the end 12 of the protection cap 11 and constructed of synthetic resin in one piece with the cap 11, for protecting the needle 7.

In detail, a tubular member 24 connected to the channel in the tubular stem 15 is joined to the end 12 and has the outer surface of its final part frusto-conical to define a male insertion element (luer type) to engage the lower support member 74 for the needle 7, which in known manner has a frusto-conical inner surface (female element) mating with the outer surface of the member 24.

On the end 12 to the side of the member 24 there is mounted said means 30, which is based on the technical solution illustrated in European patent application No. 692271 dated May 17, 1995 claiming Italian priority dated Jun. 23, 1994 relating to a protection device for a syringe needle.

In detail, the means 30 comprises an upper plate-like element 31 positioned adjacent but not secured to the needle 7 and foldable on itself substantially about a first folding axis A substantially parallel and relatively close to the axis of the needle 7. The upper element 31 is in the form of a substantially flat, relatively thin plate having a vertical folding region 32 of lesser thickness defining the first axis of rotation A.

The means 30 also comprises an element 33 for securing the support member 74 of the needle 7 to the upper element 31 such that the upper element 31 can be rotated substantially about a second folding axis B transverse to the axis of the tubular stem 15.

The protection means 30 can assume a first operating configuration in which the upper element 31 is folded on itself about the first axis A, with its two fins 31a and 31b facing each other in mutual contact, and with the upper portion of the needle enclosed between these two fins, but without the point of the needle 7 projecting from the folded element (as shown in FIG. 6).

The element 31 is sufficiently rigid not to undergo deformation such that the point of the needle 7 projects externally from the upper element when in its first operating configuration, with normal use of the needle.

The protection means 30 can also assume a second operating configuration (not shown in the figures) in which, by rotating the upper element 31 relative to the needle 7 about said second axis B, the needle projects forwards from said upper element. When in said configuration the needle 7 can be inserted into the patient's body.

The securing element 33 is rigidly joined to the lower side of the upper element 31 and to the end 12 of the cap 11, and extends to the side of the member 74. Said securing element 33 has a folding region of lesser thickness which defines said second axis of rotation B. The securing element 33 also comprises a portion 34 shaped to define an elastic means which tends to maintain the position of the upper element 31 stable when in the second operating configuration.

In the upper portion 31 there are provided means 35 and 36 for retaining together the two mutually facing fins 31a and 31b of the upper element 31 when this is in the first operating configuration. The retaining means 35 defines a projection positioned on one fin to be snap-inserted, by pressing, into a corresponding cavity (defined by the other means 36) provided in the other fin in a facing position.

Numerous modifications of a practical and applicational nature can be made to the device of the invention, but without leaving the scope of the inventive idea as claimed hereinafter.

What is claimed is:

1. A device for withdrawing and transferring body liquids which comprises a protection cap defining a concavity, and a thin sharp-ended tubular stem joined to the cap and projecting into said concavity, the tubular stem being connected, by an elastically flexible tube external to the cap, to means for penetrating the human body or body liquid containers, the device being suitable for use in combination with sample tubes to be inserted into the concavity in the cap and having an interior chamber under vacuum and closed by a yieldable elastomeric plug able to seal an aperture produced by the tubular stem, the device further comprising a clamping means projecting upwardly from the upper end of the protection cap and operated manually to close and open the passageway through the tube, such clamping means comprising a rigid first projecting element, projecting from the upper surface of the cap and having for the tube a bearing region placed against the tube, and a second element bendable on itself, having an upper portion thereof normally tending to return upwards, and having, opposite the first element, a pressing end which when the upper portion is left free to move upwards, presses and squeezes the tube against the bearing region of the first element to close its passage, the downward rotation of the upper portion of the second element causing said pressing end to withdraw from the bearing region.

2. The device for withdrawing and transferring body liquids as claimed in claim 1, wherein when in a position such as to close the passage through the tube against the bearing region, the upper portion of the second element lies substantially perpendicular to the axis of the tube.

3. The device for withdrawing and transferring body liquids as claimed in claim 1, wherein the clamping means comprises means for halting the upper portion in a closure position, the clamping means being formed such that said halting of said upper portion occurs slightly beyond the position in which the end begins to close the passage through the tube.

4. The device for withdrawing and transferring body liquids as claimed in claim 1, wherein the upper portion of the second element comprises, in one piece with the upper portion, a manually operated lever extending beyond said pressing end and possessing a slot through which the tube and the first element pass.

5. The device for withdrawing and transferring body liquids as claimed in claim 1, wherein the clamping means is constructed of synthetic resinous material in one piece with the cap.

* * * * *